(12) United States Patent
Barraud et al.

(10) Patent No.: US 11,083,991 B2
(45) Date of Patent: Aug. 10, 2021

(54) INSTALLATION AND METHOD FOR THE TREATMENT BY MEMBRANE PERMEATION OF A GAS STREAM WITH THE ASPIRATION PRESSURE OF THE SECOND PERMEATE ADJUSTED

(71) Applicant: L'Air Liquide, Societe Anonyme pour l'Etude et l'Exploitation des Procedes Georges Claude, Paris (FR)

(72) Inventors: Francois Barraud, Sassenage (FR); Jean-Marc Chareyre, Sassenage (FR)

(73) Assignee: L'Air Liquide Societe Anonyme Pour L'Etude Et L'Exploitation Des Procedes Georges Claude, Paris (FR)

( * ) Notice: Subject to any disclaimer, the term of this patent is extended or adjusted under 35 U.S.C. 154(b) by 0 days.

(21) Appl. No.: 16/712,373

(22) Filed: Dec. 12, 2019

(65) Prior Publication Data

US 2020/0188841 A1 Jun. 18, 2020

(30) Foreign Application Priority Data

Dec. 14, 2018 (FR) ...................... 1872937

(51) Int. Cl.
 *C07C 7/144* (2006.01)
 *B01D 53/22* (2006.01)
 *B01D 53/30* (2006.01)
(52) U.S. Cl.
 CPC ........... *B01D 53/226* (2013.01); *B01D 53/30* (2013.01); *C07C 7/144* (2013.01); *B01D 2053/221* (2013.01)
(58) Field of Classification Search
 CPC ........ B01D 2256/245; B01D 2257/504; B01D 2258/05; B01D 2311/04; B01D 2311/14; B01D 53/225; B01D 53/226; C10L 2290/10; C10L 2290/548; C10L 3/104; Y02C 20/40
 See application file for complete search history.

(56) References Cited

U.S. PATENT DOCUMENTS

2015/0336046 A1* 11/2015 Ungerank ............. B01D 53/22
 95/8
2018/0223205 A1 8/2018 Mitariten
2020/0261843 A1* 8/2020 Barraud ............... B01D 53/225

FOREIGN PATENT DOCUMENTS

FR          3 010 640     3/2015
WO    WO 2014/121964    8/2014

OTHER PUBLICATIONS

French Search Report and Written Opinion for FR 1872937, dated Oct. 24, 2019.

* cited by examiner

*Primary Examiner* — Sharon Pregler
(74) *Attorney, Agent, or Firm* — Christopher J. Cronin

(57) ABSTRACT

Installation for membrane permeation treatment of feed gas containing methane and carbon dioxide that includes first, second, and third membrane separation units. The permeate from the first membrane separation unit is fed to the third membrane separation unit and the retentate from the first membrane separation unit is fed to the second membrane separation unit. The aspiration pressure of the second permeate is adjusted with a compressor according to the aspiration pressure of the second permeate before recycling thereof to the feed gas flow fed to the first membrane separation unit.

4 Claims, 1 Drawing Sheet

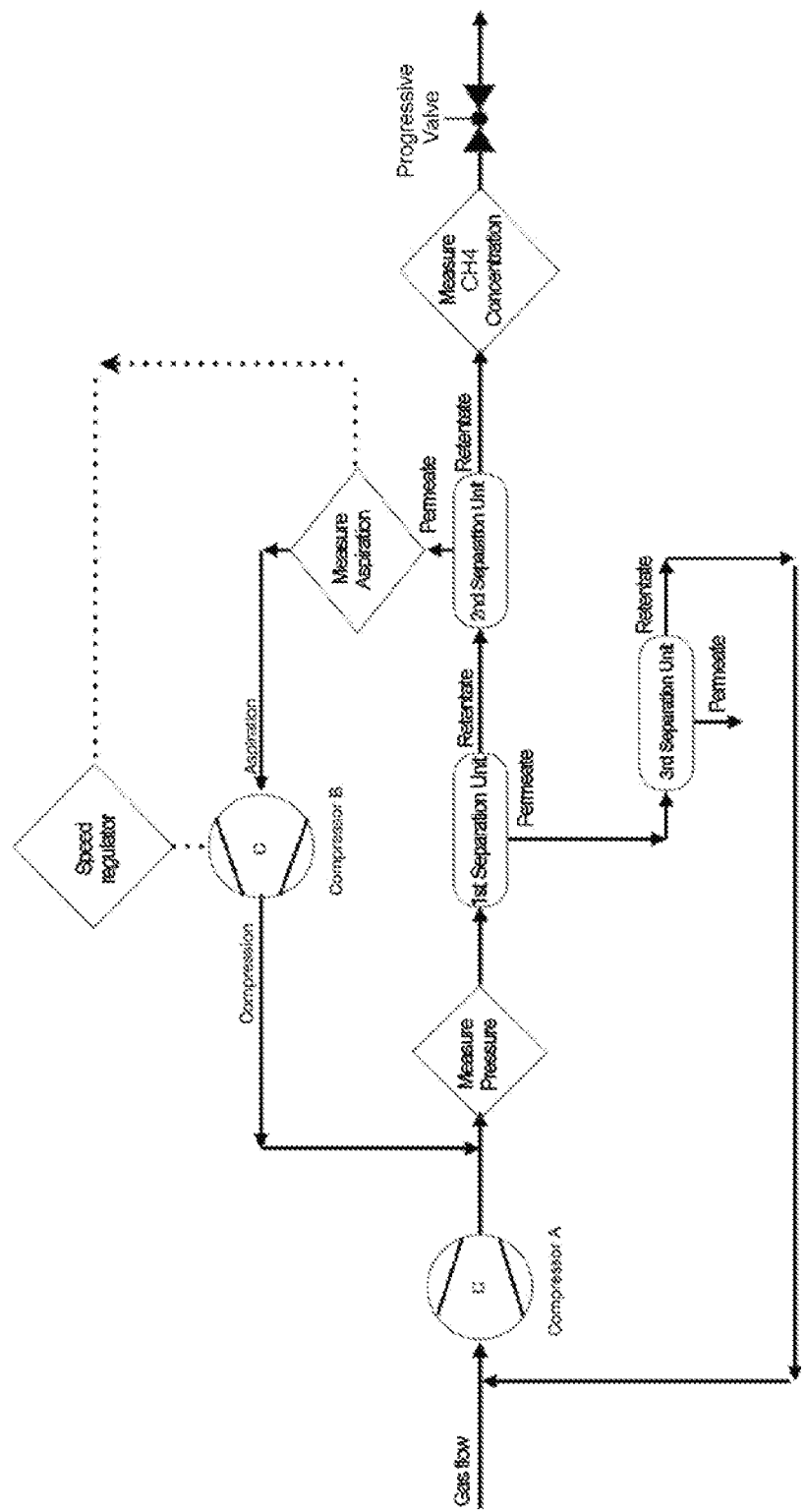

INSTALLATION AND METHOD FOR THE TREATMENT BY MEMBRANE PERMEATION OF A GAS STREAM WITH THE ASPIRATION PRESSURE OF THE SECOND PERMEATE ADJUSTED

CROSS-REFERENCE TO RELATED APPLICATIONS

This application claims the benefit of priority under 35 U.S.C. § 119 (a) and (b) to French patent application No. FR 1872937, filed Dec. 14, 2018, the entire contents of which are incorporated herein by reference.

BACKGROUND

Field of the Invention

The present invention relates to an installation for the treatment by membrane permeation of a gas stream containing at least methane and carbon dioxide in order to produce a methane-rich gas stream, of which the methane content meets the requirements of its use and to a method for controlling such an installation.

It relates in particular to the purification of biogas, with the aim of producing biomethane in accordance with the specifications for injection into a natural gas network.

Related Art

Biogas is the gas produced as organic matter breaks down in the absence of oxygen (aerobic fermentation), also referred to as methanization. This may be natural breakdown—it is thus found in marshland or in discharges from household waste—but the production of biogas may also result from the methanization of waste in a dedicated reactor referred to as a methanizer or digester.

Because of its chief constituents—methane and carbon dioxide—biogas is a powerful greenhouse gas; at the same time, it also constitutes a source of renewable energy that is appreciable in the context of the increasing scarcity of fossil fuels.

Biogas contains mainly methane ($CH_4$) and carbon dioxide ($CO_2$) in proportions that can vary according to the way in which it is obtained, but also contains, in smaller proportions, water, nitrogen, hydrogen sulphide, oxygen and other organic compounds, in trace form.

Depending on the organic matter that has been broken down and on the techniques used, the proportions of the components differ, although on average biogas contains, in the dry gas, from 30 to 75% methane, from 15 to 60% $CO_2$, from 0 to 15% nitrogen, from 0 to 5% oxygen and trace compounds.

Biogas is put to profitable use in various ways. It may, after light treatment, be put to profitable use near the production site in order to supply heat, electricity or mixture of both (cogeneration); the high carbon dioxide content reduces its calorific value, increases the cost of compression and transport and limits the economic benefit of putting it to profitable use in this way nearby.

Purifying the biogas to a greater degree allows it to be put to broader use, in particular, extensive purification of the biogas yields a biogas that has been purified to the specifications of natural gas and which can be substituted for the latter; biogas thus purified is known as "biomethane". Biomethane thus supplements the natural gas resources with a renewable proportion produced within the territories; it can be put to exactly the same uses as natural gas of fossil origin. It can be fed into a natural gas network, a vehicle filling station; it can also be liquefied and stored in the form of liquefied natural gas (LNG) etc.

The ways in which the biomethane is put to profitable use are determined according to the local context: local energy requirements, possibilities for putting it profitable use as a biomethane fuel, and whether there is a natural gas transport or distribution network nearby, in particular. By creating synergy between the various parties operating in a given territory (agriculture, industry, civic authorities), the production of biomethane assists the territories in acquiring greater self-sufficiency in terms of energy.

There are a number of stages that need to be gone through between collecting the biogas and obtaining the biomethane, the end-product that can be compressed or liquefied.

In particular, there are several stages needed prior to treatment which is aimed at separating the carbon dioxide in order to produce a stream of purified methane. A first stage is to compress the biogas which has been produced and brought in at atmospheric pressure, and this compression can be obtained—in the conventional way—using a compressor. The next stages are aimed at ridding the biogas of its corrosive components which are hydrogen sulphide and the volatile organic compounds (VOCs), the technologies used for this are, in the conventional way, pressure swing adsorption (PSA) and activated carbon capture. Next comes the stage which involves separating the carbon dioxide in order ultimately to obtain methane at the purity required for its subsequent use.

Carbon dioxide is a contaminant typically present in natural gas and it is common practice to need to remove it. Varying technologies are used for this depending on the situation; among these, membrane technology performs particularly well when the $CO_2$ content is high; and it is therefore used for separating the $CO_2$ present in biogas originating from released gases or plant or animal waste digesters.

Membrane gas-separation methods used for purifying a gas, whether they employ one or several membrane stages, need to be able to produce a gas at the required quality, at a low cost, while at the same time minimizing the losses of the gas that is to be put to profitable use. Thus, in the case of biogas purification, the separation performed is chiefly a $CH_4/CO_2$ separation which needs to allow the production of a gas containing, depending on its use, more than 85% $CH_4$, preferably more than 95% $CH_4$, more preferably more than 97.5% $CH_4$, while minimizing the $CH_4$ losses in the residual gas and the cost of purification, the latter to a large extent being associated with the electricity consumption of the device that compresses the gas upstream of the membranes.

It is preferable for the natural gas network to receive a stream of methane at a methane concentration that is constant, so that the equipment that uses the biomethane can operate uniformly.

On that basis, one problem that arises is that of providing an installation that makes it possible to obtain a stream of methane at a constant concentration.

SUMMARY OF THE INVENTION

One solution of the present invention is an installation for the membrane permeation treatment of a feed gas flow containing at least methane and carbon dioxide, comprising:

a compressor A for compressing the feed gas flow, a first membrane separation unit able to receive the gas flow coming from the compressor and to supply a first permeate and a first retentate, a second membrane separation unit able to receive the first retentate and to supply a second permeate and a second retentate, a third membrane separation unit able to receive the first permeate and to supply a third permeate and a third retentate, at least one measurement means for measuring the aspiration pressure of the second permeate in the second membrane unit, and at least one compressor B for aspirating the second permeate and adjusting the aspiration pressure of the second permeate according to the aspiration pressure measured before recycling the second permeate into the feed gas flow downstream of the compressor A, with each membrane separation unit comprising at least one membrane that is more permeable to carbon dioxide than to methane. Typically, the at least one measurement means for measuring the aspiration pressure is a pressure sensor.

BRIEF DESCRIPTION OF THE FIGURES

FIG. 1 depicts an example of an installation according to the invention.

DETAILED DESCRIPTION OF THE INVENTION

Depending on the case, the installation according to the invention may have one or more of the following features:

at least one measurement means for measuring the $CH_4$ concentration in the second retentate, and at least one pressure adjustment means for adjusting the pressure of the feed gas flow depending on the $CH_4$ concentration measured, the at least one measurement means for measuring the $CH_4$ concentration typically being a $CH_4$ analyzer.

the adjustment means for adjusting the pressure of the feed gas flow is a compressor or a progressive shut-off and pressurizing valve.

the third retentate is recycled to the compressor used for compressing the feed gas flow.

the membranes used in the membrane separation units have the same selectivity.

The present invention also relates to a method for controlling an installation as defined in the invention, comprising the following steps:

a step of measuring the aspiration pressure of the second permeate, a step of comparing this measurement with a fixed setpoint value, and a step of adjusting the aspiration pressure of the second permeate by the compressor B in order to keep the pressure value equal to the setpoint value.

As the case may be, the method according to the invention can exhibit one or more of the following features:

in the adjustment step, the compressor B is accelerated or decelerated; note that an acceleration of the compressor B will lead to a decrease in the pressure level in the membranes, and a deceleration of the compressor B will lead to an increase in the pressure level in the membranes;

the measurement, comparison and adjustment steps are carried out automatically by data transmission means;

said method comprises: a step of measuring the $CH_4$ concentration in the second retentate, a step of comparing this measurement against a setpoint value, and a step of adjusting the pressure of the feed gas flow in such a way as to reduce the determined discrepancy;

the pressure of the feed gas flow is adjusted using the compressor A or using a progressive cut-off and pressurizing valve.

the adjustment step for adjusting the feed gas flow involves increasing or decreasing the pressure;

the comparison step and the adjustments step are performed automatically by data transmission and data processing means;

the feed gas flow is biogas.

A data transmission and data processing means may for example be an industrial processor of the programmable controller type.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing i.e. anything else may be additionally included and remain within the scope of "comprising." "Comprising" is defined herein as necessarily encompassing the more limited transitional terms "consisting essentially of" and "consisting of"; "comprising" may therefore be replaced by "consisting essentially of" or "consisting of" and remain within the expressly defined scope of "comprising".

"Providing" in a claim is defined to mean furnishing, supplying; making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or about another particular value. When such a range is expressed; it is to be understood that another embodiment is from the one particular value and/or to the other particular value, along with all combinations within said range.

All references identified herein are each hereby incorporated by reference into this application in their entireties; as well as for the specific information for which each is cited.

What is claimed is:

1. The method for controlling membrane permeation treatment of a feed gas flow containing at least methane and carbon dioxide, comprising the following steps:

providing an installation that comprises: a compressor A for compressing the combined flows of feed gas and a third retentate, a first membrane separation unit able to receive the compressed combined flow of feed gas and third retentate that is admixed with a second permeate and to supply a first permeate and a first retentate, a second membrane separation unit able to receive the first retentate and to supply the second permeate and a second retentate, a third membrane separation unit able to receive the first permeate and to supply a third permeate and the third retentate, and at least one compressor B for aspirating the second permeate, feeding the aspirated second permeate to the compressed combined flows of the feed gas and the third retentate, and adjusting the aspiration pressure of the second permeate, wherein each membrane separation unit comprises at least one membrane that is more permeable to carbon dioxide than to methane;

measuring the aspiration pressure of the second permeate at a location in between the second membrane separation unit and the compressor B;

comparing the measured aspiration pressure with an associated setpoint value; and adjusting the aspiration pressure of the second permeate by the compressor B in order to keep the pressure value equal to the setpoint value associated with the aspiration pressure.

2. The method of claim 1, wherein, in the adjustment step, the compressor B is accelerated or decelerated.

3. The method of claim 1, wherein the measurement, comparison and adjustment steps are carried out automatically by data transmission means.

4. The method of claim 1, wherein the feed gas flow is biogas.

* * * * *